(12) United States Patent
Cho et al.

(10) Patent No.: US 6,488,696 B1
(45) Date of Patent: Dec. 3, 2002

(54) CHILL FRAME FOR LASERS

(75) Inventors: George Cho, Hopkinton; Anthony P Burns, Medway; Roger P. Veilleux, Marlboro, all of MA (US)

(73) Assignee: Cynosure, Inc., Chelmsford, MA (US)

( * ) Notice: Subject to any disclaimer, the term of this patent is extended or adjusted under 35 U.S.C. 154(b) by 0 days.

(21) Appl. No.: 09/399,416

(22) Filed: Sep. 20, 1999

(51) Int. Cl.$^7$ ................................................. A61N 5/00
(52) U.S. Cl. ............................. 607/89; 607/89; 607/90; 607/93; 606/9; 606/10; 606/13
(58) Field of Search ....................................... 606/8–18

(56) References Cited

U.S. PATENT DOCUMENTS 3,821,510 A * 6/1974 Muncheryan ................. 606/22
5,400,602 A * 3/1995 Chang et al. .................. 62/293

* cited by examiner

*Primary Examiner*—David M. Shay
(74) *Attorney, Agent, or Firm*—Don Halgren

(57) ABSTRACT

The present invention comprises an assembly for the single-hand manipulation of a light treatment device and a chilled air supply on a skin light-treatment site. The assembly comprises an elongated frame member having a first end and a second end. The frame member also has an upper portion and a lower portion, the upper portion having an elongated channel therealong for receipt of a light emitting optics for emitting a light beam therefrom. The lower portion has a bore extending therethrough for passage of chilled air from a chilled air source. The bore may be arranged to direct chilled air at an angle with respect to the light beam to chill the site. The assembly includes a handpiece tip member arranged at the second end of the frame assembly and maybe integral therewith. A flexible chilled air supply hose made of light weight foam material and reinforced with an expandable sleeve member connects a refrigeration unit to the frame assembly.

13 Claims, 4 Drawing Sheets

CHILL FRAME FOR LASERS

BACKGROUND OF THE INVENTION

1. Field of the Invention

This invention relates to laser arrangements, and more particularly to manipulable, hand-held frames for supporting both lasers and laser-target skin-chilling devices.

2. Prior Art

Laser treatment of human anatomy have become routine in doctors' offices. Such laser use has been adapted for treatment of skin, hair, blood vessels, eyes, and wounds. In the application of lasers to skin however, the skin temperature may reach as high as 80 degrees centigrade on the skin surface. This can become quite painful to the patient receiving such treatment. Cooling the skin or surface of the patient before, during and subsequent to the laser application minimizes such patient injury. Additionally, cooling of the skin provides an analgesic effect, thereby minimizing the pain sensation during a light or laser energy treatment.

Heretofore, cooling of the patients' skin has been accomplished by a separate, hand-held cooling air jet, held in one hand, while the laser device is held in the other hand of the treating physician. This makes it difficult to manipulate the patient as well as the multiple devices utilized to treat that patient. The laser devices typically have to be spaced from the patient's skin a specific distance. Simultaneous, multiple skin treatment devices only make it more difficult and cumbersome to treat that patient.

An improvement in the skin-chilling apparatus included a cold air attachment angularly disposed on an L-shaped frame at the tip of the laser device. The chilled air, supplied by a separate hose, was directed directly at the target site of the laser beam. The nozzle for the chilled air supply and its attached hose of this prior art device is arranged at an angle, so as to be somewhat cumbersome because of the different supply conduits of the laser and of the chilled air hose are spread out and not arranged neatly in a parallel arrangement.

It is an object of the present invention, to provide a frame arrangement for supporting both a chilled air supply, and a laser device in a single, unitary, one-hand manipulable structure, to provide optimum cooling and lasing simultaneously.

It is a further object of the present invention to provide an improvement over the laser and skin chilling apparatus of the prior art.

It is still a yet further object of the present invention, to provide a frame arrangement for a laser device and a chilled air supply conduit for cooling the skin of a patient as well as the space bar of the laser frame apparatus.

BRIEF SUMMARY OF THE INVENTION

The present invention comprises a frame arrangement for enclosing both a laser device such as laser optics, and a chilled air conduit, for the application of a laser beam and chilled air onto the treatment surface of a patient. Such combined laser treatment and chilling is utilized for laser hair removal, laser treatment of vascular lesions, tattoo removal, skin resurfacing, wrinkle removal, scar treatment, skin stretch mark treatment, or any other dermatological application.

The light and chilled air frame arrangement of the present invention comprises an elongated housing frame having a first end and a second end. The elongated housing frame has an upper portion having a generally cylindrically shaped channel or slot arranged therethrough. The generally cylindrically shaped channel or slot extends the entire length of the elongated housing frame and is opened on both ends thereof. The slot or channel is arranged to support a light-emitting optics device, such as a laser light carrying handpiece secured therewithin. The handpiece or optical arrangement is connected to a laser via a flexible light energy carrying optical fiber.

The elongated housing frame has a lowermost portion with an elongated bore extending therethrough. The elongated bore is generally parallel to the longitudinal axis of the cylindrically shaped slot or channel in the uppermost portion of the elongated housing frame. The bore extending through the lowermost portion of the elongated housing frame has an angled discharge port in the second end of the elongated housing frame. The first end of the elongated housing frame has a chilled air supply hose attached thereto, in communication with the bore extending through the lowermost portion of that frame. The chilled air supply hose is communicatively attached to a refrigeration unit, so as to permit the supply of chilled air through the flexible hose, and into the elongated bore extending through the lower portion of the elongated housing frame. The discharge port in the second end of the elongated housing frame may be angled to direct the chilled air towards the target which is the patent's skin at the intersection of the laser beam and that skin.

An elongated, handpiece tip may be threadably received in an opening in the upper end of a handpiece adapter plate. The handpiece adapter plate is a generally oval-shaped plate having a light port arranged therethrough, the light port being in alignment with the opening at the second end of the elongated housing frame to permit a light beam to pass therethrough. The adapter plate also has a lower chilled-air port, which is in alignment with the discharge port of the cooled air supply bore in the lower portion of the elongated housing frame. The handpiece adapter plate is removably received in a curvilinear channel arranged about the second end of the elongated housing frame. The channel has a shoulder or lip, to secure the adapter plate within that channel. In a further embodiment, the handpiece tip may be integral with the elongated housing frame. Such an assembly may be molded plastic or metal.

In operation of the present invention, the treating physician would actuate the refrigeration and chilled-air unit, to supply chilled air through the flexible expandable-sleeve reinforced, light weight foam tubing leading to the first end of the elongated housing frame. The flexible hose from the refrigeration unit is a foam material, to permit flexibility, and allow ready manipulation thereof. The light weight foam hose is reinforced with an expandable sleeve to prevent kinking. The treating physician would have a foot or hand actuatable switch for the generation of light, such as a laser light, from the light emitting optics arranged within the cylindrically shaped slot/channel in the elongated housing frame. Constant or intermittent bursts of light may be directed onto the patient's skin, through the elongated housing frame arrangement. The frame arrangement is spaced from that patient's skin by the length of the handpiece tip attached to the handpiece adapter plate. Chilled air would be directed through the bore of the elongated housing frame, and discharged finally, through the discharge port in the second end of the elongated housing frame, and out the chilled air port of the handpiece adapter plate. The direction of the chilled air in one embodiment may be such to be angled with respect to the longitudinal axis of the light emitted from the light emitting optics, and also to chill the distal end of the handpiece tip. This permits the chilling of the patient's treatment area, such as the skin, by the chilled air as well as providing a chilling of that patient's treatment area by the distalmost end of the tip. The angle of the discharge port with respect to the longitudinal axis of the light device preferably lies in the range of between 20 to 60 degrees.

Thus there has been shown a unique light and chilled air supply arrangement with easy manipulation of both of those components for treatment of a patients skin, by a single hand of the treating physician. The elongated frame arrangement also provides multiple sources of cooling of that patient's skin by virtue of the blast of chilled air itself, as well as the chilled tip. In a further embodiment, the distal end of the handpiece tip may have an imprint arrangement such as a U-shaped or circular-shaped frame element thereon, to supply a "footprint" to the patient's treatment site. That tip footprint arrangement provides a contact heat sink in addition to that heat dissipating arrangement provided by the direct blast of the chilled air.

The invention thus comprises an assembly for the single-hand manipulation of a light treatment device and a chilled air. supply on a skin light-treatment site. The assembly comprises an elongated frame member having a first end and a second end. The frame member also has an upper portion and a lower portion. The upper portion has an elongated slot therealong for receipt of a light emitter for emitting a light beam therefrom. The lower portion has a bore extending therethrough for passage of chilled air from a chilled air source. The bore is arranged to direct chilled air at an angle with respect to the light beam to chill the site. The assembly includes a removable handpiece tip member arranged at the second end of the frame assembly. The frame includes a curvilinear channel and shoulder arranged on the second end thereof, for receipt of a handpiece adapter plate, the plate supporting the tip member. The handpiece adapter plate has a light port and a chilled air port arranged to permit passage of light and chilled air therethrough from a flexible, reinforced chilled air supply hose. A refrigerated air source is in communication with the air supply hose. The bore is arranged to chill both the tip member and the treatment site on the patient. A light energy source is in communication with the light emitter optics in the elongated frame housing. A tip footprint member may be arranged onto the second end of the frame. The tip in either embodiment may be integral with the elongated frame for simplicity of manufacture.

The invention also comprises a method of treating a skin site on a patient using light and chilled air comprising the steps of: arranging an elongated frame housing having a first end and a second end, and an upper portion and a lower portion; placing an elongated channel along the upper portion and a bore along the lower portion; arranging a light emitter in the elongated channel to emit a beam of light at the second end of the fame; connecting a flexible refrigerated chilled air supply hose to a first end of the bore; attaching a tip member at the second end of the fame housing; and directing the bore for the chilled air to a treatment site on the patient and to a distal end of the tip member. The method includes emitting light from the light source and onto a treatment site on the patient, cooling the treatment site by the tip member. The method may include the step of replacing the tip member by a further tip member to define a footprint on the treatment site.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
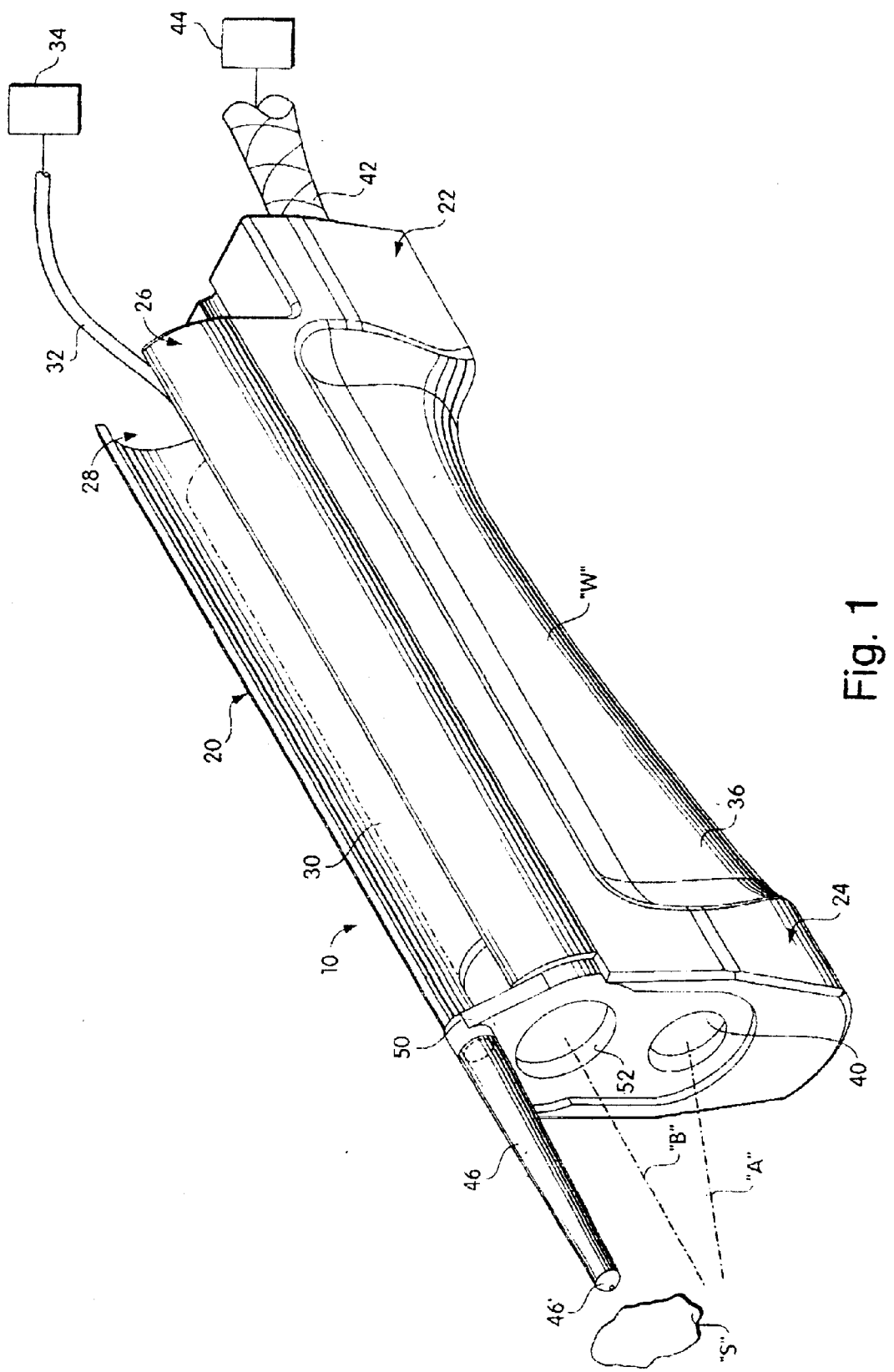
FIG. 1 is a prospective view of a laser and chilled-air control frame arrangement, constructed according to the principles of the present invention.

Referring now to the drawings in detail, and particularly to FIG. 1, there is shown the present invention which comprises a frame arrangement 10 for enclosing both a laser device 12 and a chilled air conduit 14, for the application of a laser beam "B" and chilled air "A" onto the treatment surface "S" of a patient. Such combined laser treatment and chilling is utilized for laser hair removal, laser treatment of vascular lesions, tattoo removal, skin resurfacing, wrinkle removal, scar treatment, skin stretch mark treatment, or any other dermatological application.

The light and chilled air frame arrangement 10 of the present invention comprises an elongated housing frame 20 having a first end 22 and a second end 24. The elongated housing frame 20 has an upper portion 26 having a light channel or generally cylindrically shaped slot 28 cut therethrough. The light channel 28 extends the entire length of the elongated housing frame 20 and is open on both ends 22 and 24 thereof. The light channel 28 may have an elongated opening 29 therealong, as shown in the figures, so as to permit access to a trigger (not shown) of a light-emitting optics device 30 supported therewithin, such as a laser light carrying handpiece. The laser device 30 would have its own flexible light carrying optical fiber cable 32 connected from the first end of the housing frame 20, the other end connected to a light source 34.

Figure 3:
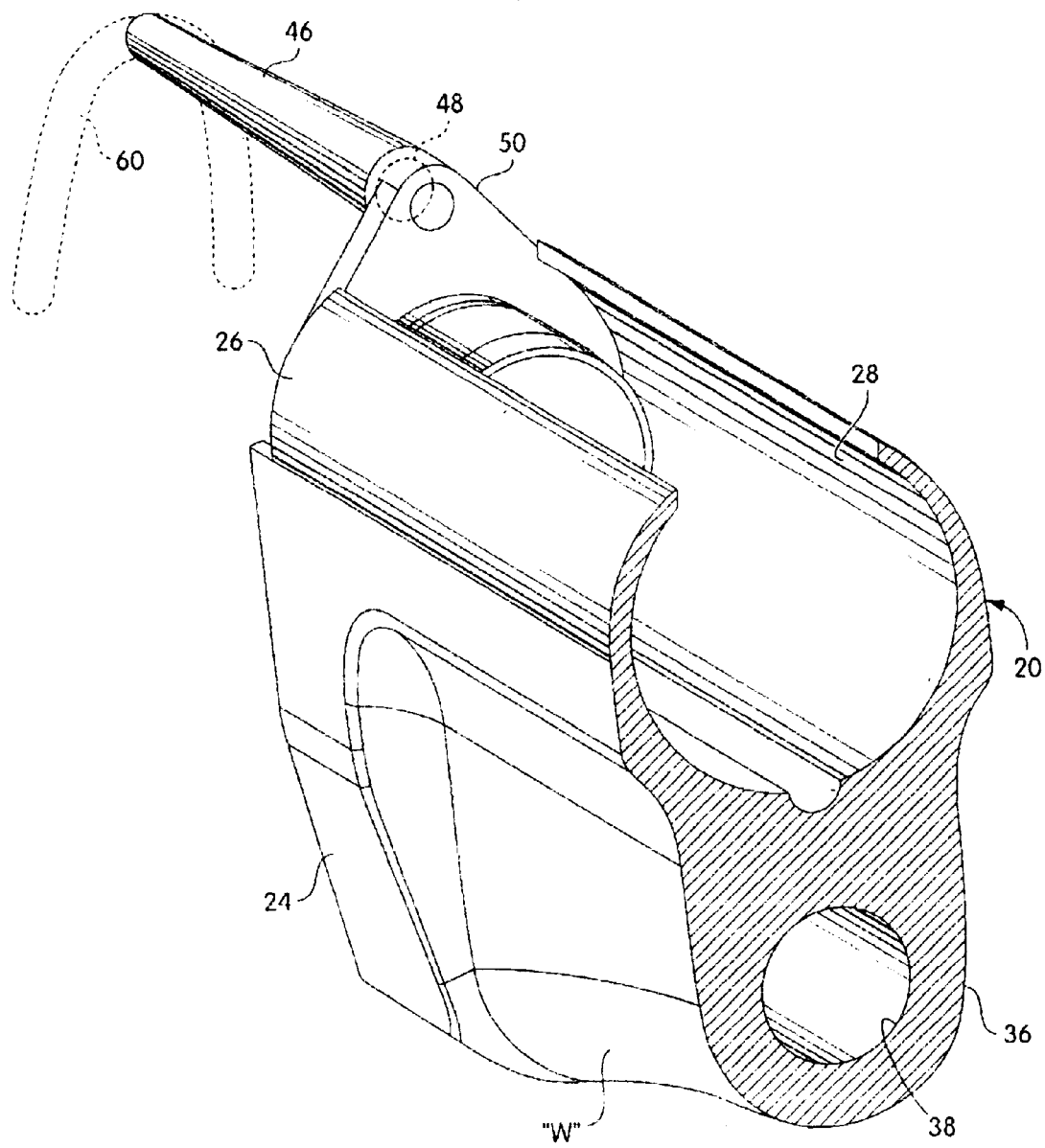
FIG. 3 is a sectional view in perspective, looking towards the second end of the frame assembly.
Figure 4:
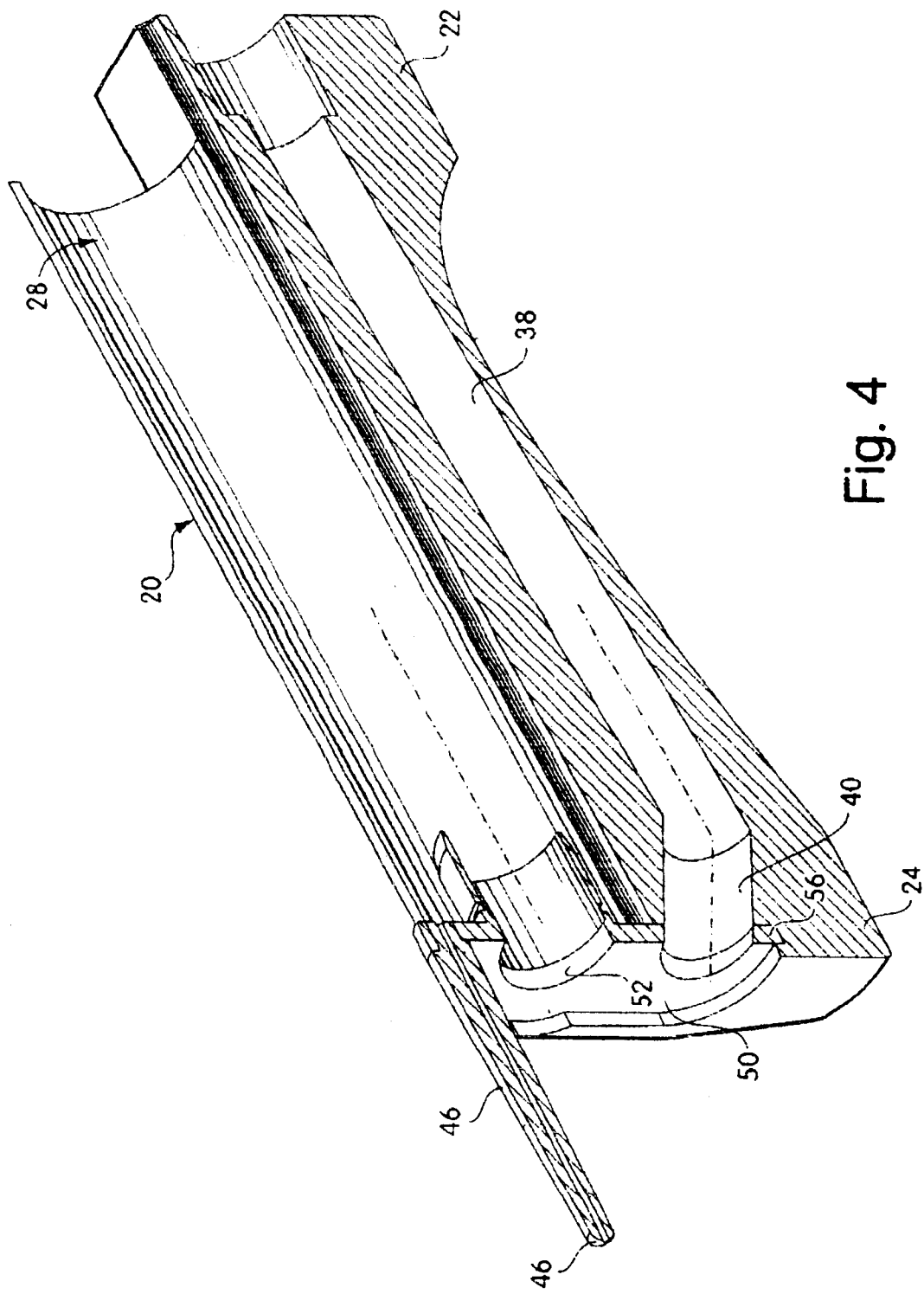
FIG. 4 is a longitudinal sectional view of the frame assembly and section.

The elongated housing frame 20 has a lowermost portion 36, as shown in FIGS. 3 and 4, of reduced width "W" for ease of gripping by the hand of the treating physician, the portion 36 also having an elongated bore 38 extending therethrough. The elongated bore 38 is generally parallel to the longitudinal axis "L" of the light channel or cylindrically shaped slot 28 in the uppermost portion 26 of the elongated housing frame 20. The bore 38 extending through the lowermost portion 36 of the elongated housing frame 20 may in one preferred embodiment, have an angled discharge port 40 in the second end 24 of the elongated housing frame 20. The first end 22 of the elongated housing frame 20 has a chilled air supply hose 42 attached thereto, in communication with the bore 38 extending through the lowermost portion 36 of that frame 20. The chilled air supply hose 42 is communicatively attached to a refrigeration unit 44, so as to permit the supply of chilled air through the flexible hose 42, and into the elongated bore 38 extending through the lower portion 36 of the elongated housing frame 20. The angled discharge port 40 in the second end 24 of the elongated housing frame 20 directs the chilled air towards the target "S" which is the patent's skin at the intersection of the laser beam "B" and that skin, or the discharge port may be in line with the bore 38.

Figure 2:
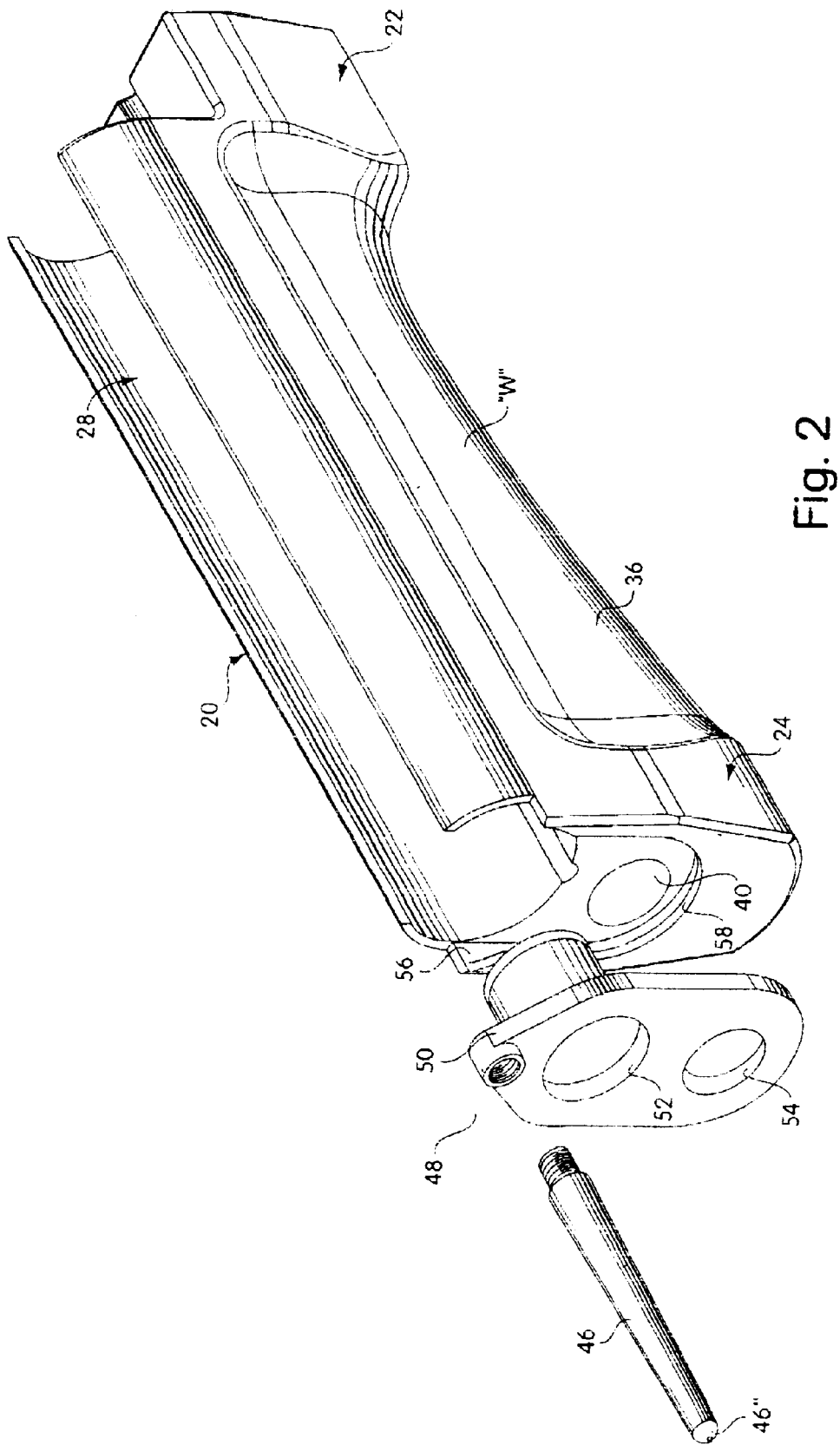
FIG. 2 is an exploded view of the invention shown in FIG. 1.

An elongated, handpiece tip 46 is threadably received in an opening 48 in the upper end of a handpiece adapter plate 50, as shown in the exploded view in FIG. 2. The handpiece adapter plate 50 is a generally oval-shaped plate having a light port 52 arranged therethrough, the light port 52 being in alignment with the opening at the second end 24 of the elongated housing frame 20 to permit a light beam "B" to pass therethrough. The handpiece plate 50 also has a lower, chilled-air port 54, which is in alignment with the discharge port 40 of the cooled air supply bore 38 in the lower portion 36 of the elongated housing frame 20. The handpiece plate 50 in one preferred embodiment, is removably received in a curvilinear channel 56 arranged about the second end 24 of the elongated housing frame 20. The channel 56 has a shoulder or lip 58, to secure the handpiece plate 50 within that channel 56.

In operation of the present invention, the treating physician would actuate the refrigeration and chilled-air unit 44, to supply chilled air through the flexible expandable-sleeve reinforced foam tubing 42 leading to the first end 22 of the elongated housing frame 20. The flexible hose 42 from the refrigeration unit 44 is made of foam material reinforced with a web-like material, which is expandable to permit flexibility, resist kinking, and allow ready manipulation thereof. The treating physician would have a foot or hand actuatable switch, not shown for clarity, to actuate the generation of light, such as a laser light, from the light emitting source. Constant or intermittent bursts of light "B" may be directed onto the patient's skin "S", through the elongated housing frame arrangement 20. The frame arrangement 20 is spaced from that patient's skin "S" by the length of the handpiece tip 46 attached to the handpiece adapter plate 50. Chilled air "A" may be directed through the bore 38 of the elongated housing frame 20, and discharged finally, through the discharge port 40 in the second end 24 of the elongated housing frame 20, and out the chilled air port 54 of the handpiece adapter plate 50. As mentioned in one aforementioned preferred embodiment, the direction of the chilled air "A" would be such to be angled with respect to the longitudinal axis of the light "B" emitted from the light emitting optics 30, and also to chill the distal end of the handpiece tip 46. This permits the chilling of the patient's treatment area "S" such as the skin by the chilled air as well as also providing a chilling of that patient's treatment area by the cooled distalmost tip 46' of the spacer member 46. The angle of the discharge port 40 with respect to the longitudinal axis of the light device 30 preferably lies in the range of between 20 to 60 degrees.

Thus there has been shown a unique light and chilled air supply arrangement with easy manipulation of both of those components for treatment of a patients skin, by a single hand of the treating physician. The elongated frame arrangement also provides multiple sources of cooling of that patient's skin by virtue of the blast of chilled air itself, as well as the chilled tip 46. In a further embodiment, the distal end of the tip member 46 may have an imprint arrangement such as a "configured" U-shaped or circular-shaped frame element 60 thereon, as exemplified in dashed lines in FIG. 3, to supply a "footprint" to the patient's treatment site. That footprint arrangement provides a contact heat sink in addition to that heat dissipating arrangement provided by the direct blast of the chilled air.

We claim:

1. An assembly for the single-hand manipulation of a light treatment device and a chilled air supply on a skin light-treatment site, said assembly comprising an elongated frame member having a first end and a second end, said frame member also having an upper portion and a lower portion, said upper portion having an elongated light channel therealong for passage of a light beam along its length said lower portion having a bore extending therethrough for passage of chilled air from a chilled air source, said bore being arranged to direct chilled air to said skin treatment site wherein said frame includes a curvilinear channel and shoulder arranged on said second end thereof for receipt of a handpiece adapted plate said plate supporting said handpiece tip members and wherein said handpiece adapted plate has a light port and a chilled air port arranged to permit passage of light and chilled air therethrough.

2. The assembly for the single-hand manipulation of a light treatment device and a chilled air supply as recited in claim 1, wherein said assembly includes a removable handpiece tip arranged at said second end of said frame assembly.

3. The assembly for the single-hand manipulation of a light treatment device and a chilled air supply as recited in claim 1, wherein said bore is arranged at an angle with respect to said light beam.

4. The assembly for the single-hand manipulation of a light treatment device and a chilled air supply as recited in claim 1, wherein said light channel has a laser optics device supported therein.

5. The assembly for the single-hand manipulation of a light treatment device and a chilled air supply as recited in claim 4, wherein said bore is arranged to chill both a tip member on said device and the treatment site on said patient.

6. The assembly for the single-hand manipulation of a light treatment device and a chilled air supply as recited in claim 1, including a flexible, expandable-sleeve reinforced, chilled air supply foam hose for supplying chilled air to said first end of said assembly.

7. The assembly for the single-hand manipulation of a light treatment device and a chilled air supply as recited in claim 5, including a tip footprint member arranged onto said second end of said frame.

8. The assembly for the single-hand manipulation of a light treatment device and a chilled air supply, as recited in claim 6, including a refrigerated air source in communication with said air supply hose.

9. The assembly for the single-hand manipulation of a light treatment device and a chilled air supply as recited in claim 6, including a light energy source in communication with said light emitter optics device in said light channel in said elongated frame housing.

10. An assembly for the single-hand manipulation of a light treatment device and a chilled air supply on a skin light-treatment site, said assembly comprising an elongated frame member having a first end and a second end, said frame member also having an upper portion and a lower portion, said upper portion having an elongated light channel therealong for receipt of a light emitting optics for emitting a light beam therefrom, said lower portion having a lower bore extending therethrough for passage of chilled air from a chilled air source, said lower bore at said second end of said elongated housing, being arranged to direct chilled air at an angle with respect to said light beam to chill said site;

said assembly including a handpiece tip member arranged at said second end of said frame assembly; said frame including a curvilinear channel and shoulder arranged on said second end thereof, for receipt of a handpiece adapter plate, said plate supporting said tip member; said plate having a light port and a chilled air port arranged to permit passage of light and chilled air therethrough; and a flexible, reinforced chilled air supply hose for supplying chilled air from a chilled air source to said housing.

11. A method of treating a skin site on a patient using light energy and chilled air comprising the steps of:

arranging an elongated frame housing having a first end and a second end, and an upper portion and a power portion;

placing an elongated light channel along said upper portion and a bore along said lower portion;

arranging a light emitting optics in said elongated light channel to emit a beam of light energy at said second end of said fame;

connecting a flexible refrigerated chilled air supply hose to a first end of said bore;

attaching a tip member at said second end of said frame housing;

directing said bore for said chilled air to a treatment site on said patient and to a distal end of said tip member; and replacing said tip member by a further configured tip member to define a footprint on said treatment site.

12. The method of treating a skin site on a patient using light energy and chilled air as recited in claim 11, comprising the step of:

emitting light from said light emitting optics device and onto a treatment site on said patient.

13. The method of treating a skin site on a patient using light energy and chilled air as recited in claim 12, comprising the step of:

cooling said treatment site by said tip member.

* * * * *